(12) United States Patent
Wakabayashi et al.

(10) Patent No.: US 8,303,508 B2
(45) Date of Patent: Nov. 6, 2012

(54) ULTRASOUND ENDOSCOPE

(75) Inventors: Katsuhiro Wakabayashi, Hachioji (JP); Hideo Adachi, Iruma (JP); Takanao Fujimura, Sagamihara (JP); Yukihiko Sawada, Yoshikawa (JP); Akiko Mizunuma, Hachioji (JP); Takuya Imahashi, Kawasaki (JP); Sunao Sato, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 474 days.

(21) Appl. No.: 12/203,795

(22) Filed: Sep. 3, 2008

(65) Prior Publication Data

US 2009/0005688 A1 Jan. 1, 2009

Related U.S. Application Data

(63) Continuation of application No. PCT/JP2007/053927, filed on Mar. 1, 2007.

(30) Foreign Application Priority Data

Mar. 3, 2006 (JP) .................................. 2006-058707
Jun. 8, 2006 (JP) .................................. 2006-160192

(51) Int. Cl.
*A61B 8/12* (2006.01)
(52) U.S. Cl. ........ 600/462; 600/463; 600/464; 600/439; 600/101
(58) Field of Classification Search ........................ None
See application file for complete search history.

(56) References Cited

U.S. PATENT DOCUMENTS

| 6,149,598 A | 11/2000 | Tanaka |
| 6,186,947 B1 | 2/2001 | Ouchi |
| 6,409,666 B1 | 6/2002 | Ito |
| 6,461,304 B1 * | 10/2002 | Tanaka et al. ................. 600/462 |
| 2004/0082883 A1 * | 4/2004 | Kohno .............................. 601/2 |

FOREIGN PATENT DOCUMENTS

| JP | 7-28867 | 4/1995 |
| JP | 08-131442 | 5/1996 |
| JP | 08-280685 | 10/1996 |
| JP | 2000-041985 | 2/2000 |
| JP | 2001-112760 | 4/2001 |
| JP | 2002-011010 | 1/2002 |
| JP | 2004-350700 | 12/2004 |
| JP | 2005-323886 | 11/2005 |
| JP | 2006-26232 | 2/2006 |

OTHER PUBLICATIONS

Extended Supplementary European Search Report dated Dec. 11, 2009.

* cited by examiner

*Primary Examiner* — Long V. Le
*Assistant Examiner* — Farshad Negarestan
(74) *Attorney, Agent, or Firm* — Scully, Scott, Murphy & Presser, P.C.

(57) ABSTRACT

An ultrasound endoscope has an ultrasound probe which is disposed at a distal end side of a distal end rigid portion configuring a distal end portion out of a flexible tube portion, a bending portion and the distal end rigid portion configuring an insertion portion, and forms an ultrasound scanning surface having a normal line in a direction orthogonal to an endoscope insertion axis L1, and a treatment instrument outlet of a treatment hole in the distal end rigid portion. The ultrasound probe is configured by a plurality of ultrasound transducers arranged in a convex circular arc shape, and a center of curvature of the plurality of ultrasound transducers is disposed at a proximal end side from the treatment instrument outlet.

9 Claims, 11 Drawing Sheets

| # ULTRASOUND ENDOSCOPE

CROSS REFERENCE TO RELATED APPLICATION

This application is a continuation application of PCT/JP2007/053927 filed on Mar. 1, 2007 and claims benefit of Japanese Applications No. 2006-058707 filed in Japan on Mar. 3, 2006, and No. 2006-160192 filed in Japan on Jun. 8, 2006, the entire contents of which are incorporated herein by their reference.

BACKGROUND OF THE INVENTION

1. Field of the Invention

The present invention relates to an ultrasound endoscope having a convex-type ultrasound probe in which an observation optical system, a treatment instrument outlet, and a plurality of ultrasound transducers are arranged at a distal end of an insertion portion of an endoscope.

2. Description of the Related Art

As an endoscope for performing ultrasound observation in a body cavity, or therapy and treatment by using treatment instruments, an ultrasound endoscope having a convex-type ultrasound probe at a distal end of the endoscope is known. The convex-type ultrasound probe is configured by arranging a plurality of ultrasound transducers in a convex circular arc shape.

As the ultrasound endoscopes having convex-type ultrasound probes, the ones disclosed in, for example, Japanese Patent Application Laid-Open Publication No. 8-131442 and Japanese Patent Application Laid-Open Publication No. 2004-350700 (see FIG. 19) are cited. In each of the ultrasound endoscopes, an observation optical system is included at a distal end rigid portion in the vicinity of an ultrasound probe, and the observation optical system has an optical axis in a diagonally forward direction.

In an ultrasound endoscope, such positional relationship as to allow observation of an inside of an observation region as an ultrasound tomography image while visually recognizing the observation region with an observation optical system is essential. In order to confirm the insertion depth or the like of a treatment instrument by an ultrasound tomography image, an ultrasound scanning range with an operation range of the treatment instrument taken into consideration is required.

Therefore, in the case of each of the observation optical systems with diagonally forward views as disclosed in Japanese Patent Application Laid-Open Publication No. 8-131442 and Japanese Patent Application Laid-Open Publication No. 2004-350700, the diagonally forward optical axis and the operation range of the treatment instrument can be contained within the ultrasound scanning range by providing an ultrasound probe at a distal end side of the distal end rigid portion.

However, in the ultrasound endoscope disclosed in Japanese Patent Application Laid-Open Publication No. 8-131442, the structure including the ultrasound probe in addition to the distal end rigid portion makes the rigid length of a so-called endoscope insertion portion.

Further, in the structure of the ultrasound endoscope disclosed in Japanese Patent Application Laid-Open Publication No. 2004-350700, a slope is provided at a distal end rigid portion, and an ultrasound probe is loaded on the slope. In this structure, the distal end rigid length is shorter as compared with the ultrasound endoscope disclosed in the Japanese Patent Application Laid-Open Publication No. 8-131442. However, in order to enable to contain the treatment instrument which is led out from a treatment instrument outlet within the ultrasound scanning range, the ultrasound endoscope disclosed in Japanese Patent Application Laid-Open Publication No. 2004-350700 is provided with an ultrasound probe in a semi-circular shape with an ultrasound scanning range at 180 degrees. In the ultrasound endoscope, the structure including the length which is twice as long as the radius of curvature of the ultrasound probe in addition to the distal end rigid portion makes the distal end rigid length.

SUMMARY OF THE INVENTION

An ultrasound endoscope of the present invention is an ultrasound endoscope having an ultrasound probe portion which is disposed at a distal end side of a distal end rigid portion configuring a distal end portion out of a flexible tube portion, a bending portion and the distal end rigid portion configuring an endoscope insertion portion, and forms an ultrasound scanning surface having a normal line in a direction orthogonal to an endoscope insertion axis, and a treatment instrument outlet of a treatment instrument inserting channel in the distal end rigid portion, in which the ultrasound probe is configured by a plurality of ultrasound transducers arranged in a convex circular arc shape, and a center of curvature of the plurality of ultrasound transducers is disposed at a proximal end side from the treatment instrument outlet.

DESCRIPTION OF THE PREFERRED EMBODIMENT(S)

Hereinafter, an embodiment of the present invention will be described in detail with reference to the drawings.

Figure 1:
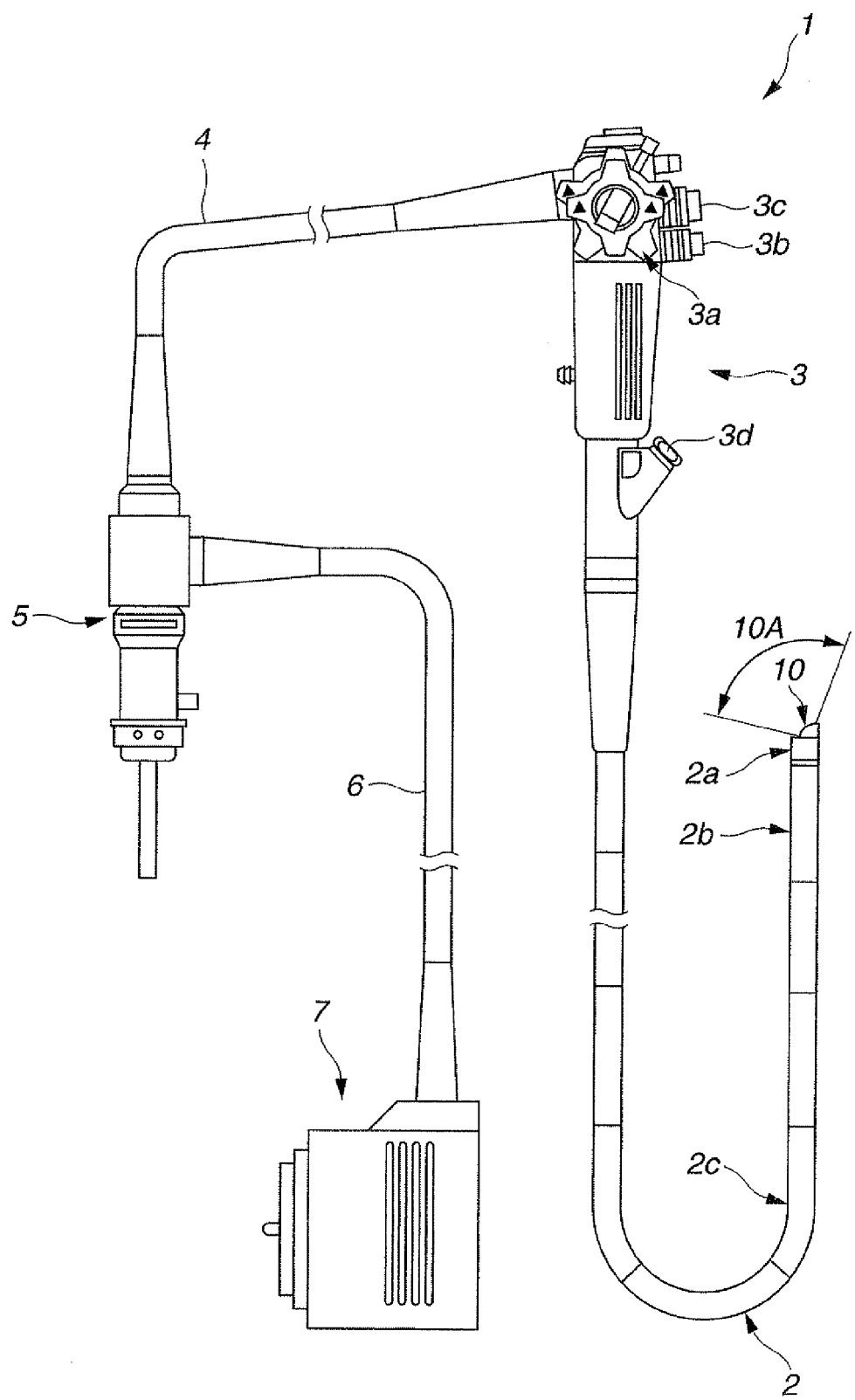
FIG. 1 is a view for explaining a configuration of an ultrasound endoscope.

With reference to FIGS. 1 to 14, an embodiment of the present invention will be described. As shown in FIG. 1, an ultrasound endoscope (hereinafter, also described as an endoscope) 1 of the present embodiment is configured by including an elongated insertion portion 2 which is inserted into a body cavity, an operation portion 3 provided at a proximal end of the insertion portion 2, and a universal cord 4 extended from a side portion of the operation portion 3. An endoscope connector 5 is provided at the other end of the universal cord 4. An ultrasound cable 6 is extended from a side portion of the endoscope connector 5. An ultrasound connector 7 is provided at the other end of the ultrasound cable 6.

The insertion portion 2 is configured by connecting a distal end rigid portion 2a formed of a rigid member, a bending portion 2b configured to be bendable, and a flexible tube portion 2c which is elongated, has flexibility, and extends from a proximal end of the bending portion 2b to a distal end of the operation portion 3, in sequence from the distal end side. The operation portion 3 is provided with an angle knob 3a for performing a bending operation. Further, the operation portion 3 is provided with an air-supply and water-supply button 3b for performing operations of air supply and water supply, and a suction button 3c for performing suction. Further, the operation portion 3 is provided with a treatment instrument insertion port 3d for introducing a treatment instrument into a body cavity.

Reference numeral 10 denotes an ultrasound unit including an ultrasound probe having a convex ultrasound scanning surface. The ultrasound unit 10 forms an ultrasound scanning range 10A for scanning in a forward direction with respect to the endoscope insertion axis direction.

Figure 2:
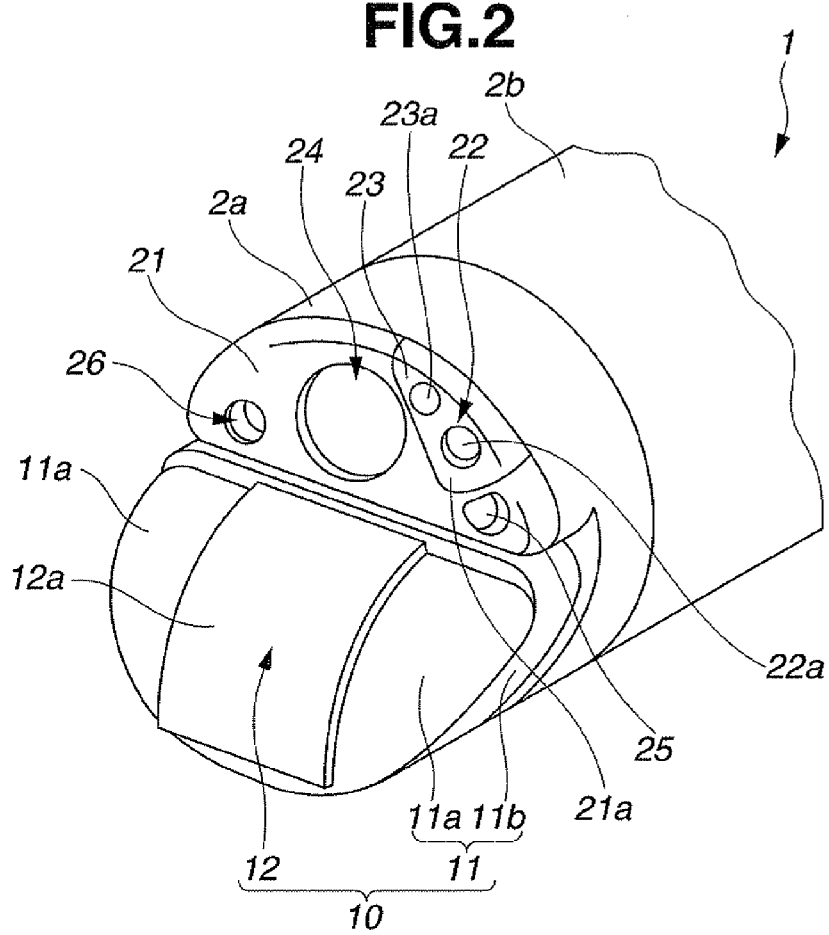
FIG. 2 is a perspective view for explaining a configuration of a distal end portion of the ultrasound endoscope.
Figure 3:
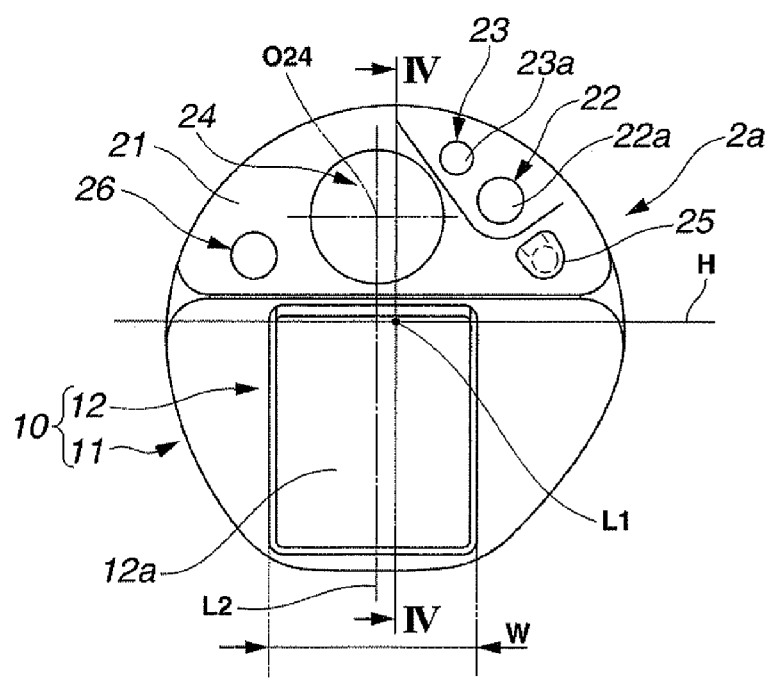
FIG. 3 is a front view of the distal end portion shown in FIG. 2 seen from a front.

As shown in FIGS. 2 and 3, the distal end rigid portion 2a of the insertion portion 2 is provided with the ultrasound unit 10 for obtaining acoustic image information by ultrasound. The ultrasound unit 10 is configured by including a nose piece 11 which is a casing, and an ultrasound probe 12. The ultrasound probe 12 is integrally placed in a notch portion formed in a substantially central portion of the nose piece 11. As shown in the drawing, a tissue abutting surface 11a configuring the nose piece 11, and an acoustic lens surface 12a of the ultrasound probe 12 are configured into a shape projected from a distal end surface 21 of the distal end rigid portion 2a.

Figure 4:
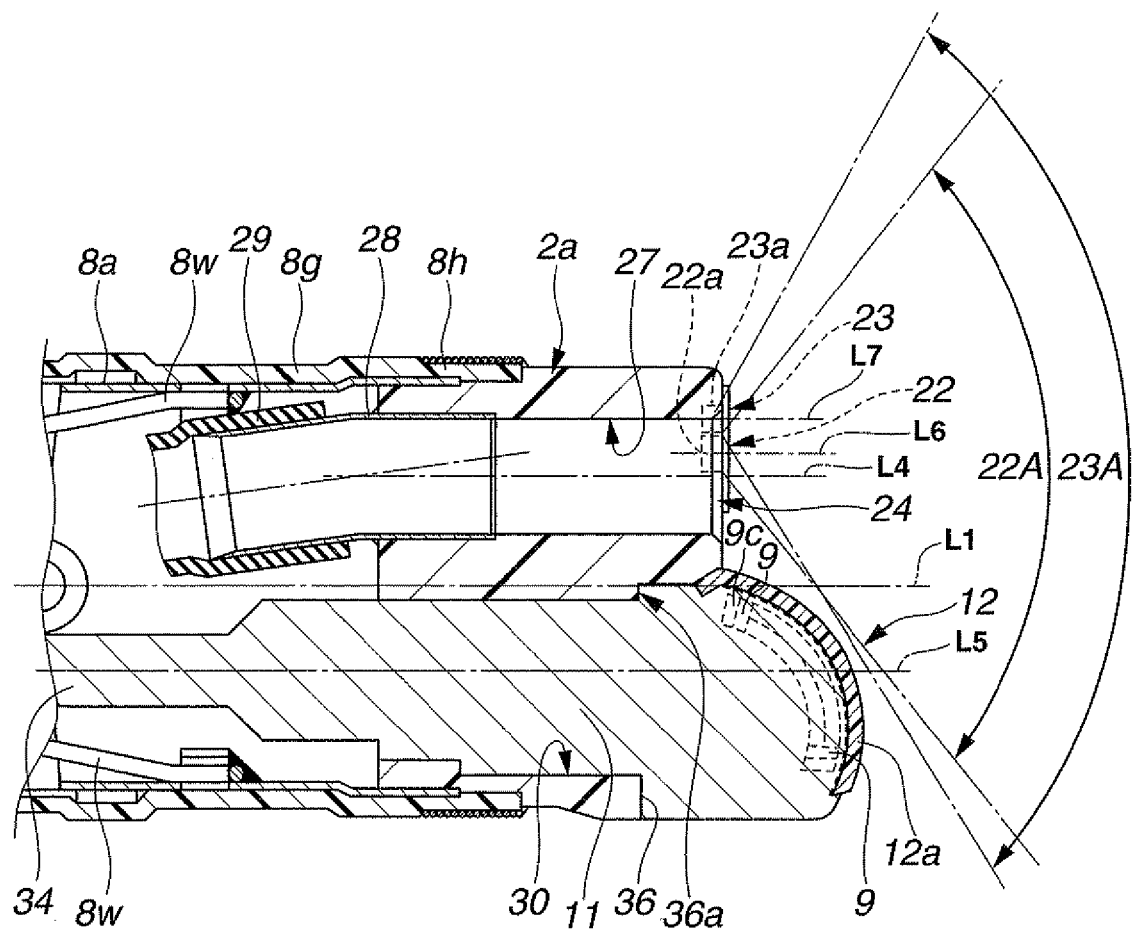
FIG. 4 is a sectional view taken along the IV-IV line in FIG. 3.
Figure 5:
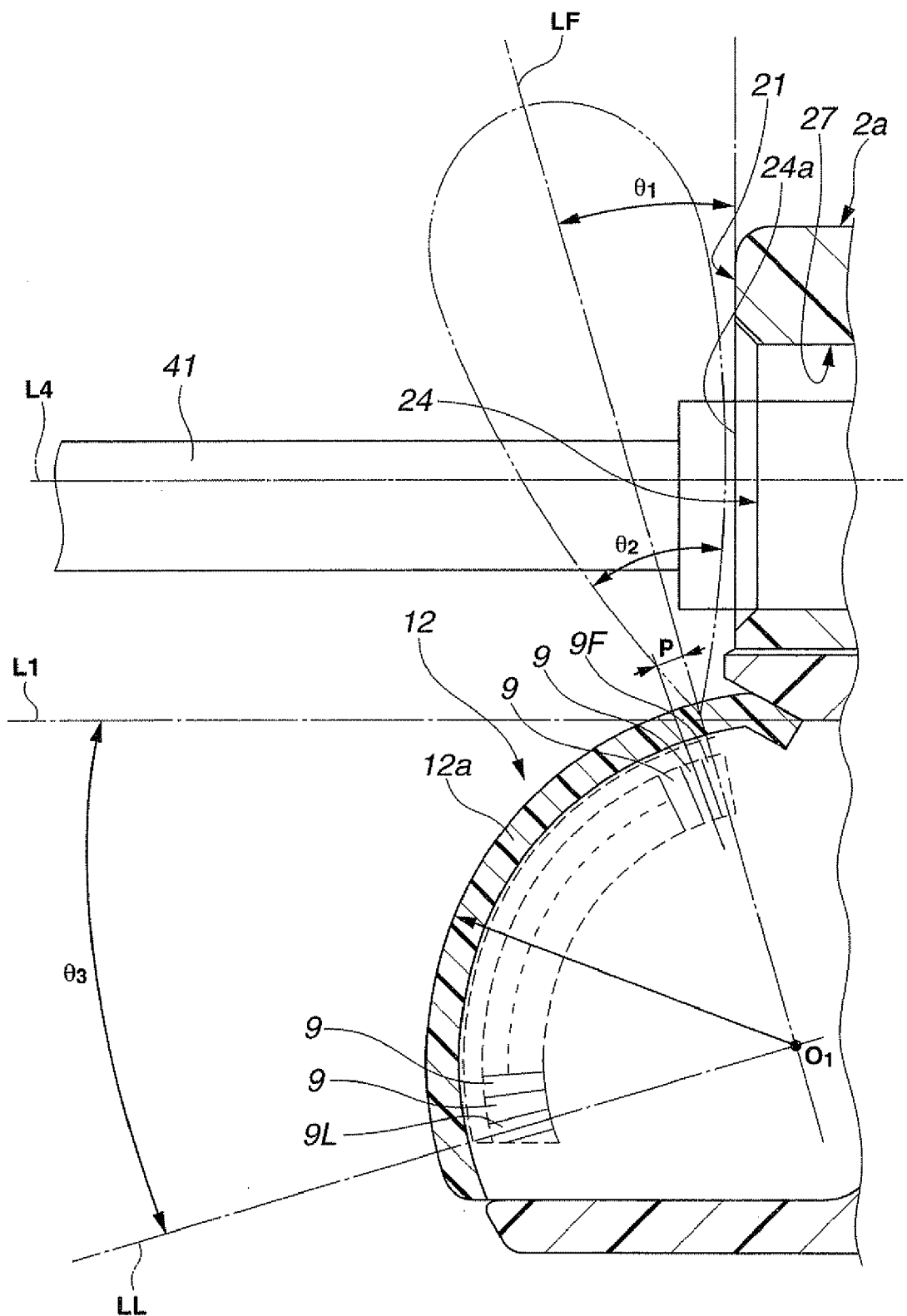
FIG. 5 is a view for explaining the relationship among an ultrasound probe configured by arranging a plurality of ultrasound transducers, an ultrasound observation region of the ultrasound probe, and a treatment instrument which is led out from a treatment instrument outlet.

As shown in FIGS. 4 and 5, the ultrasound probe 12 is configured by, for example, a plurality of ultrasound transducers 9 and the acoustic lens 12a. The plurality of ultrasound transducers 9 are arranged to form a convex circular arc.

Meanwhile, the distal end surface 21 of the distal end rigid portion 2a is provided with an observation window 22a configuring an observation optical system 22, an illumination window 23a configuring an illumination optical system 23, a treatment instrument outlet 24 from which a treatment instrument such as a puncture needle is led out, an air-supply and water-supply nozzle 25 for ejecting a fluid such as water and air toward the observation window 22a, and an auxiliary water-supply channel port 26 for supplying water forward, as shown in FIGS. 2 and 3. Instead of providing the auxiliary water-supply channel port 26, the auxiliary water-supply channel port 26 may be configured as a second treatment instrument outlet.

A center O24 of the treatment instrument outlet 24 is arranged on the same straight line as a center line L2 of the ultrasound probe 12 so that the treatment instrument which is led out from the treatment instrument outlet 24 is contained within the ultrasound scanning range 10A obtained by the ultrasound probe 12.

The observation window 22a, the illumination window 23a and the air-supply and water-supply nozzle 25 are disposed together, for example, at the right side in the drawing, with respect to the treatment instrument outlet 24, and disposed outside the ultrasound scanning range 10A. Out of the observation window 22a, the illumination window 23a and the air-supply and water-supply nozzle 25, the position of the air-supply and water-supply nozzle 25 is set to be the farthest position from the ultrasound scanning range 10A. Further, in the present embodiment, the disposed positions of the illumination window 23a, the observation window 22a and the air-supply and water-supply nozzle 25 are disposed on one straight line in consideration of the purpose of improving the observation performance and cleaning performance, and reducing the outside diameter dimension of the endoscope distal end portion.

The observation window 22a has an observation visual field range of the observation optical system 22, for which reference should be made to the range of reference numeral and character 22A shown by the dashed line in FIG. 4. The illumination window 23a has an illumination light irradiation range of the illumination optical system 23, for which reference should be made to the range of reference numeral and character 23A shown by the two-dot chain line in FIG. 4. The observation visual field range 22A and the illumination light irradiation range 23A are configured not to contain the ultrasound probe 12 in the ranges.

The observation window 22a, and the illumination window 23a are provided in an observation distal end surface 21a configured to be slightly projected from the distal end surface 21. Further, the auxiliary water-supply channel port 26 is on one surface side at an opposite side from the other surface side, on which the observation window 22a, the illumination window 23a and the air-supply and water-supply nozzle 25 are disposed, with the treatment instrument outlet 24 between the one surface side and the other surface side, and the auxiliary water-supply channel port 26 is disposed outside the ultrasound scanning range 10A. When the auxiliary water-supply channel port 26 is configured as the second treatment instrument outlet, the diameter dimension of the channel is set in accordance with the treatment instrument to be used.

Thereby, manipulation using two treatment instruments can be performed under endoscope observation. Therefore, the configuration of efficiently performing diagnosis and treatment by combining the treatment instrument which is projected from the second treatment instrument outlet and used under endoscope observation and the treatment instrument which is projected from the treatment instrument outlet 24 and used under ultrasound diagnosis can be realized.

As shown in FIG. 4, a distal end bending piece 8a configuring the bending portion 2b is connected and fixed to a proximal end side of the distal end rigid portion 2a. A plurality of bending pieces not illustrated are connected to the distal end bending piece 8a. A straight line connecting a center of the bending portion 2b configured by connecting the bending pieces is an endoscope insertion axis L1.

Distal end portions of vertical and lateral bending wires 8w are fixedly provided at predetermined positions of the distal end bending piece 8a. Accordingly, by an operator properly operating the angle knob 3a, the bending wire 8w corresponding to the operation is pulled or loosened so that the bending portion 2b performs a bending operation. The plurality of bending pieces are covered with a bending rubber 8g. A distal end portion of the bending rubber 8g is integrally fixed to the distal end rigid portion 2a by a winder joining portion 8h.

The distal end surface 21 of the distal end rigid portion 2a, and the observation distal end surface 21a are configured to be orthogonal to the endoscope insertion axis L1. In the distal end rigid portion 2a, a treatment instrument inserting channel hole (hereinafter, abbreviated as a treatment instrument hole) 27 configuring the treatment instrument outlet 24, and a disposition hole 30 are formed.

The distal end rigid portion 2a includes a through hole provided with the observation optical system, a through hole provided with the illumination optical system, a through hole for supplying air and water, which supplies a fluid to be ejected from the air-supply and water-supply nozzle 25, a through hole configuring the auxiliary water-supply channel port 26 and the like though not illustrated, in addition to the holes 27 and 30.

A center axis L4 in a longitudinal direction of the treatment instrument hole 27 is formed substantially parallel with the endoscope insertion axis L1. A center axis L5 in a longitudinal direction of the disposition hole 30 is formed substantially parallel with the endoscope insertion axis L1. Further, an optical axis L6 of the observation optical system and an optical axis L7 of the illumination optical system included in the ultrasound endoscope 1 are also parallel with the endoscope insertion axis L1.

Accordingly, the observation optical system included in the ultrasound endoscope 1 of the present embodiment is a so-called direct-viewing type in which the observation visual field is set at a front in a forward direction, in other words, an insertion direction at a forward side of the endoscope insertion axis L1.

One end portion of a tube connecting pipe 28 formed by being inclined by a predetermined amount is allowed to communicate with a proximal end side of the treatment instrument hole 27. One end portion of a channel tube 29 configuring the treatment instrument inserting channel communicates with the other end portion of the tube connecting pipe 28. The other end portion of the channel tube 29 communicates with the treatment instrument insertion port 3d.

The treatment instrument which is inserted via the treatment instrument insertion port 3d smoothly moves inside the channel tube 29, the tube connecting pipe 28 and the treatment instrument hole 27 and is led outside from the treatment instrument outlet 24. The treatment instrument which is led outside from the treatment instrument outlet 24 is projected in the forward direction which is the insertion direction of the insertion portion 2 to be parallel with the endoscope insertion axis L1.

More specifically, in the state in which a distal end portion of a puncture needle is disposed inside the treatment instrument hole 27, as the treatment instrument, for example, when a needle tube configuring the puncture needle is projected, the needle tube moves from the treatment instrument outlet 24 toward the front in the forward direction observed through the observation window 22a to be substantially parallel with the endoscope insertion axis L1.

Meanwhile, the disposition hole 30 is provided in the distal end rigid portion 2a. The ultrasound unit 10 is fitted in the disposition hole 30, and an abutting surface of the nose piece 11 and a contact surface 36 of the distal end rigid portion 2a abut on each other, whereby positioning of the ultrasound unit 10 with respect to the disposition hole 30 is performed. From the other end side of the ultrasound unit 10, an ultrasound cable 34 connected to the ultrasound probe 12 is led out.

An outer shape extending to the distal end from the contact surface 36 of the distal end rigid portion 2a, that is, a surface shown by reference numeral and character 11b in FIG. 2 includes an elevation width W of the ultrasound probe 12 and the abutting surface 11a, and is set to have substantially the same dimension as the outside dimension of the distal end of the distal end rigid portion 2a as shown in FIG. 2.

Figure 8:
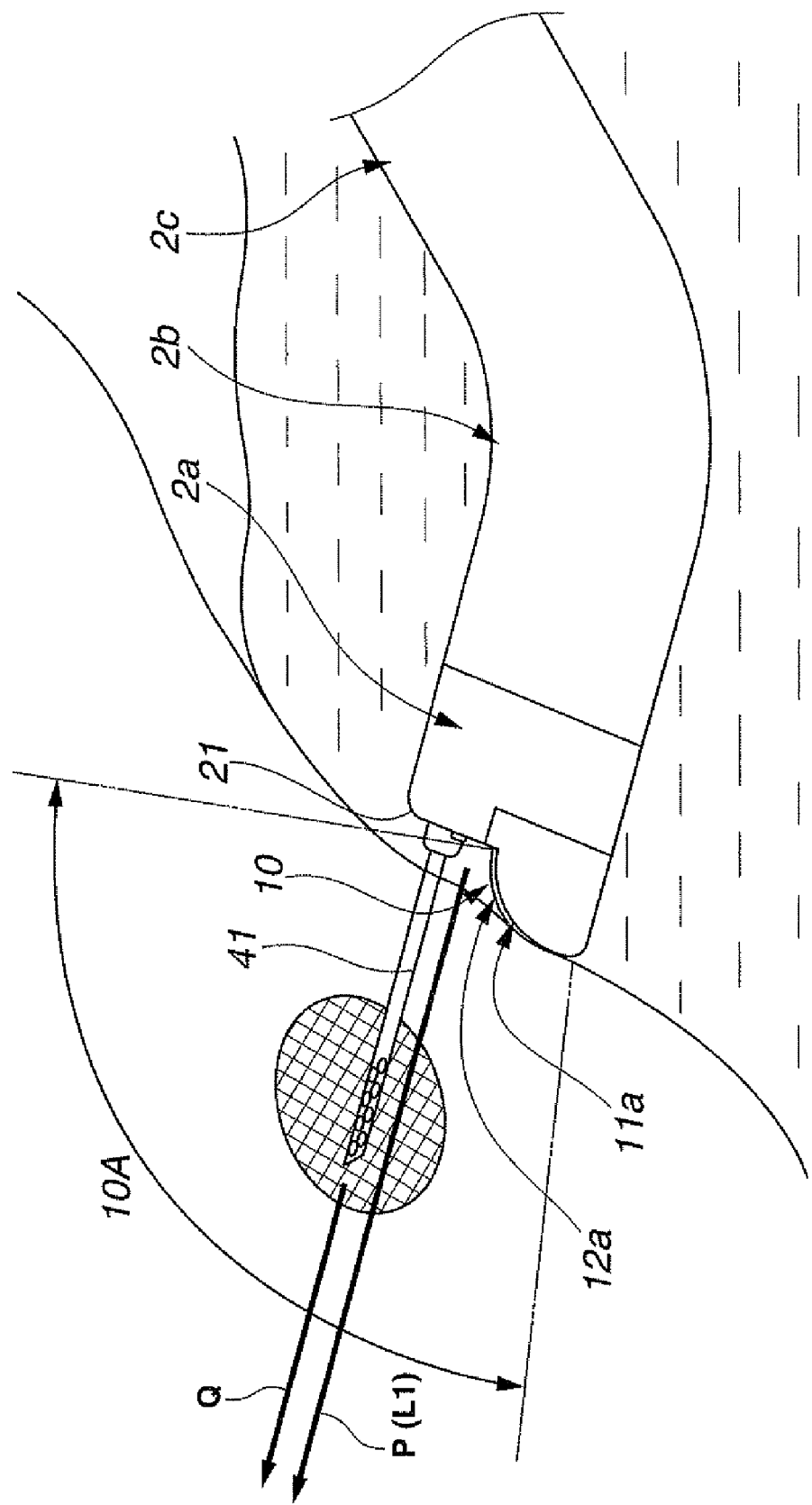
FIG. 8 is a view for explaining relationship between a tissue abutting surface of a nose piece and an acoustic lens surface of the ultrasound probe.

Therefore, when the ultrasound unit 10 is pushed against a body tissue on the occasion of ultrasound observation, the power of the operator grasping the operation portion 3 in the direction of the endoscope insertion axis L1 is reliably transmitted to the ultrasound unit 10. As a result, the tissue abutting surface 11a and the acoustic lens surface 12a can be uniformly brought into close contact with the body tissue as shown in FIG. 8. In this manner, the tissue abutting surface 11a and the acoustic lens surface 12a of the ultrasound unit 10 are pushed against the body tissue in the stable state, and a favorable ultrasound observation image can be obtained.

The ultrasound probe 12 shown in FIGS. 4 and 5 is configured by arranging a plurality of ultrasound transducers 9 in each of which, for example, a backing material, a piezoelectric transducer, a matching layer and an acoustic lens are stacked in layer. The plurality of ultrasound transducers 9 from a first ultrasound transducer 9F which is disposed at the position closest to the treatment instrument outlet 24 and irradiates ultrasound to a final ultrasound transducer 9L which is at the farthest position when counted from the treatment instrument outlet 24 are arranged at predetermined pitches p. As shown in FIG. 5, a center of curvature O1 of the circular arc of the ultrasound probe 12 is configured to be located at a proximal end side from an opening surface 24a of the treatment instrument outlet 24 provided in the distal end rigid portion 2a. For the ultrasound transducer 9, an MUT (Micromachined Ultrasound Transducer) element may be used instead of the piezoelectric element.

By providing the center of curvature O1 of the circular arc of the ultrasound probe 12 at the proximal end side from the opening surface 24a of the treatment instrument outlet 24 like this, the distal end rigid length of the endoscope 1 is shortened. Therefore, insertability of the endoscope 1 into a body cavity is improved. Further, since the configuration in which the ultrasound probe 12 is not disposed within the observation visual field range of the endoscope 1 is adopted, the problem that a part of an endoscope image is lost by the ultrasound probe 12 is solved. Further, the ultrasound probe 12 is not within the illumination light irradiation range of the endoscope 1, and therefore, a part of illumination light is not shielded by the ultrasound probe 12. Thus, illumination light spreads into the observation visual field range of the endoscope 1, and a favorable endoscope image can be obtained.

In the ultrasound probe 12, a direction of a center axis LF of a sound ray of the first ultrasound transducer 9F is set to incline to the distal end side by an angle $\theta 1$ with respect to the distal end surface 21, with the distal end surface 21 of the distal end rigid portion 2a, more specifically, the distal end surface 21 including the treatment instrument outlet 24 as the reference.

Further, when the direction of the center axis LF of the sound ray of the first ultrasound transducer 9F is set to incline to the distal end side by the angle $\theta 1$, a spread angle $\theta 2$ of the first ultrasound transducer 9F is taken into consideration More specifically, the angle $\theta 1$ is set so that at least a part of the distal end rigid portion 2a which is made of the material that can reflect ultrasound, for example, a metal or a rigid resin, at least a part of the air-supply and water-supply nozzle 25 or the like does not enter within the spread angle enclosed by the two-dot chain line in FIG. 5. The angle θ1 is set to be larger than at least θ/2, that is half the spread angle θ2.

Figure 6:
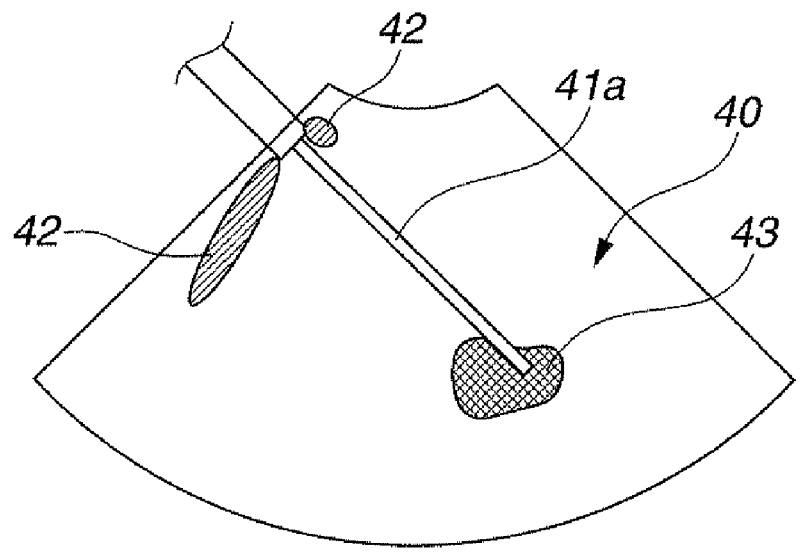
FIG. 6 is a view showing an ultrasound image example in which an artifact appears.
Figure 7:
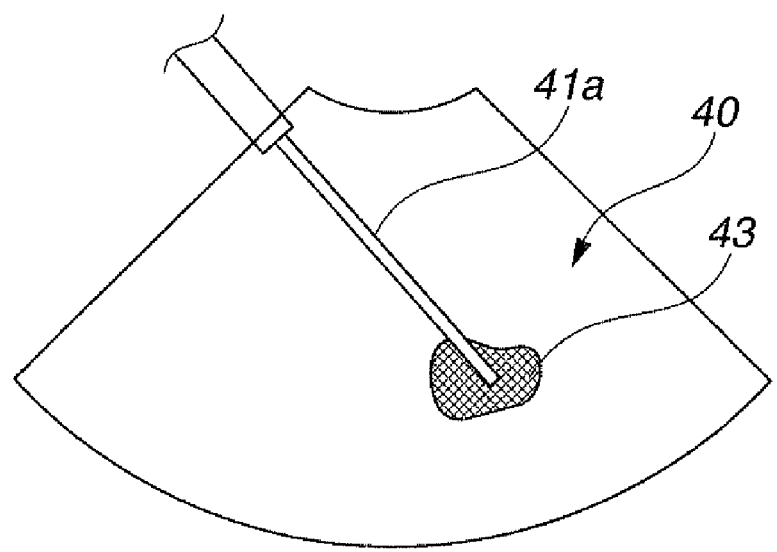
FIG. 7 is a view showing an ultrasound image example visualized with the ultrasound probe shown in FIG. 5.

When the distal end rigid portion 2a is within the range of the spread angle, an artifact 42 as shown in FIG. 6 appears. However, according to the configuration of the present embodiment, an artifact does not appear, and a treatment instrument ultrasound image 41a is clearly visualized in an ultrasound image 40 as shown in FIG. 7. Namely, the treatment instrument ultrasound image 41a until the treatment instrument 41 punctures a lesion 43 from the state in which the treatment instrument 41 is slightly projected from the treatment instrument outlet 24 is clearly visualized in the ultrasound image 40. By obtaining such favorable visibility, the treatment instrument 41 can be accurately introduced to the lesion 43.

Meanwhile, a direction of a center axis LL of a sound ray of the final ultrasound transducer 9L is set to be parallel with the endoscope insertion axis L1, or to diverge by an angle θ3 as the center axis LL extends forward.

Figure 9:
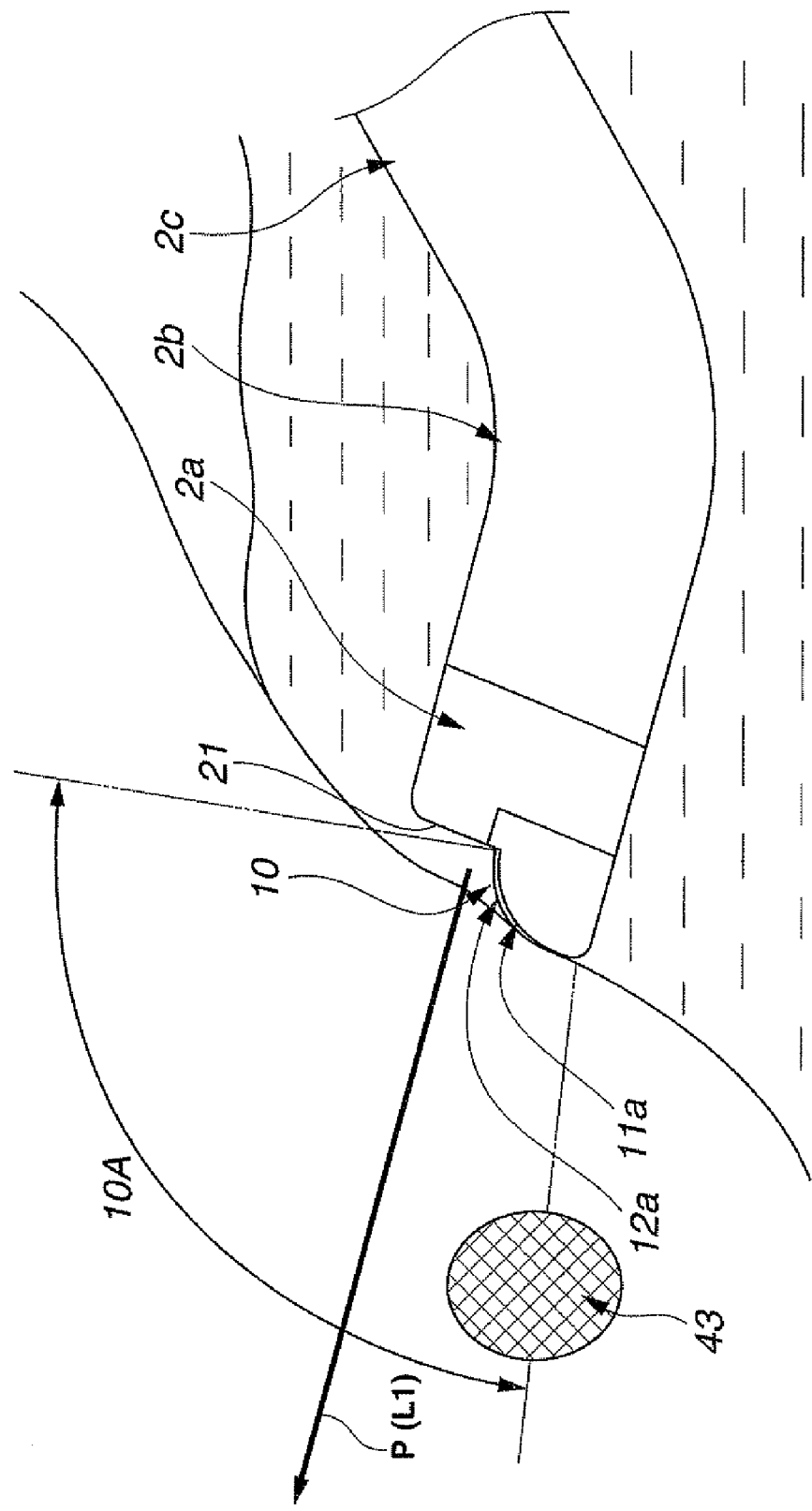
FIG. 9 is a view for explaining a state in which a lesion is present in the vicinity of a boundary of the ultrasound observation region of the ultrasound endoscope.
Figure 10:
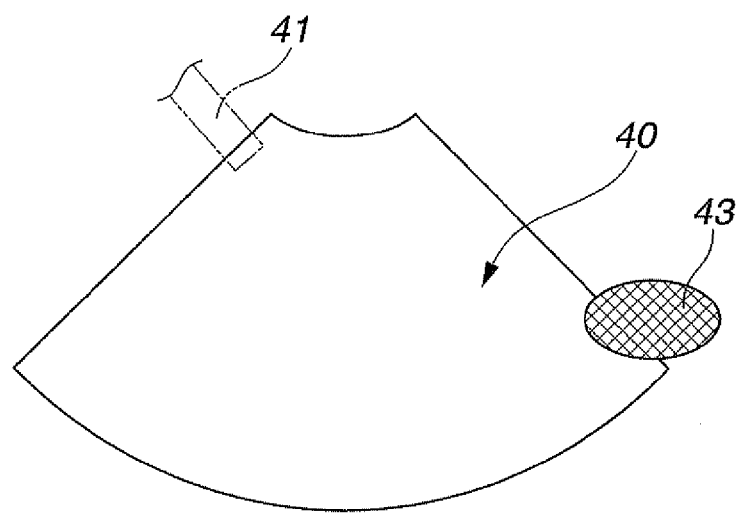
FIG. 10 is a view showing an ultrasound image in the observation state shown in FIG. 9.

As a result, when the treatment instrument 41 which is projected from the treatment instrument outlet 24 is projected forward substantially in parallel with the endoscope insertion axis L1, the treatment instrument 41 continues to move in the vicinity of the center of the ultrasound scanning range 10A. Further, even when the endoscope 1 moves before puncture due to pulsation or the like, and the lesion 43 is present outside the endoscope insertion axis L1 as shown in FIG. 9, for example, the lesion 43 is located at a boarder of the ultrasound scanning range 10A, whereby the lesion 43 is displayed at an edge in the ultrasound image 40 as shown in FIG. 10.

Namely, even if the relative position of the endoscope 1 and the lesion 43 deviates, the ultrasound scanning range 10A is present up to the angle exceeding the endoscope insertion axis L1, and therefore, sight of the lesion 43 can be prevented from being lost. Accordingly, an operator can easily correct the positional deviation of the endoscope 1 and the lesion 43 by performing a manual operation, and introduces the treatment instrument 41 to the lesion 43 after the correction.

In the above described embodiment, the elevation width of the ultrasound probe 12 is set at the dimension W as shown in FIG. 3. In other words, the elevation widths of the plurality of ultrasound transducers 9 configuring the ultrasound probe 12 are uniformly set at the dimension W. On the other hand, in the ultrasound probe 12A shown in FIGS. 11 and 12, an elevation width WF of the first ultrasound transducer 9F and an elevation width WL of the final ultrasound transducer 9L are set at different dimensions.

Figure 11:
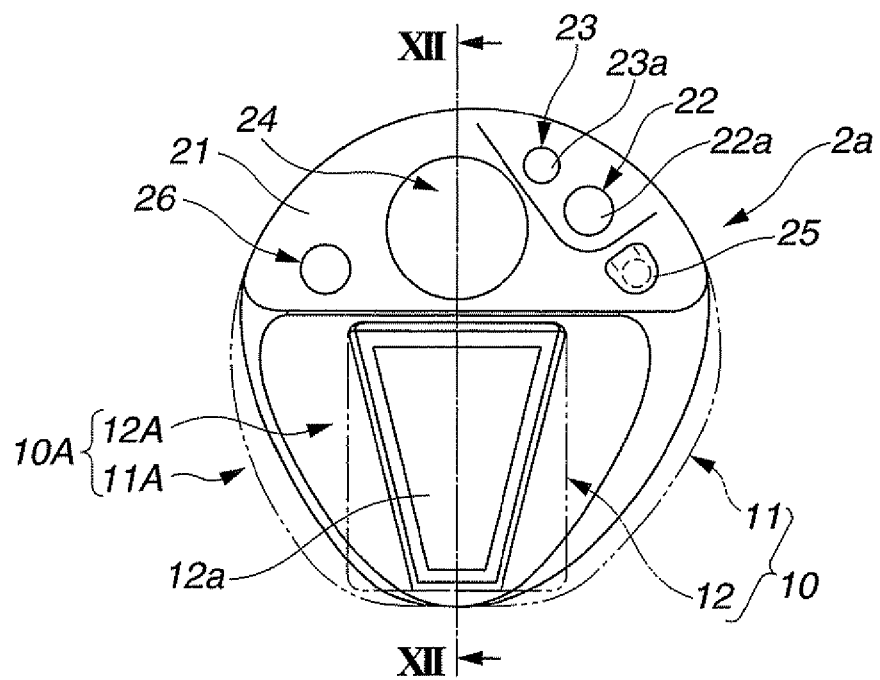
FIG. 11 is a front view of the distal end portion including the ultrasound probe of which elevation width continuously changes, seen from the front.
Figure 12:
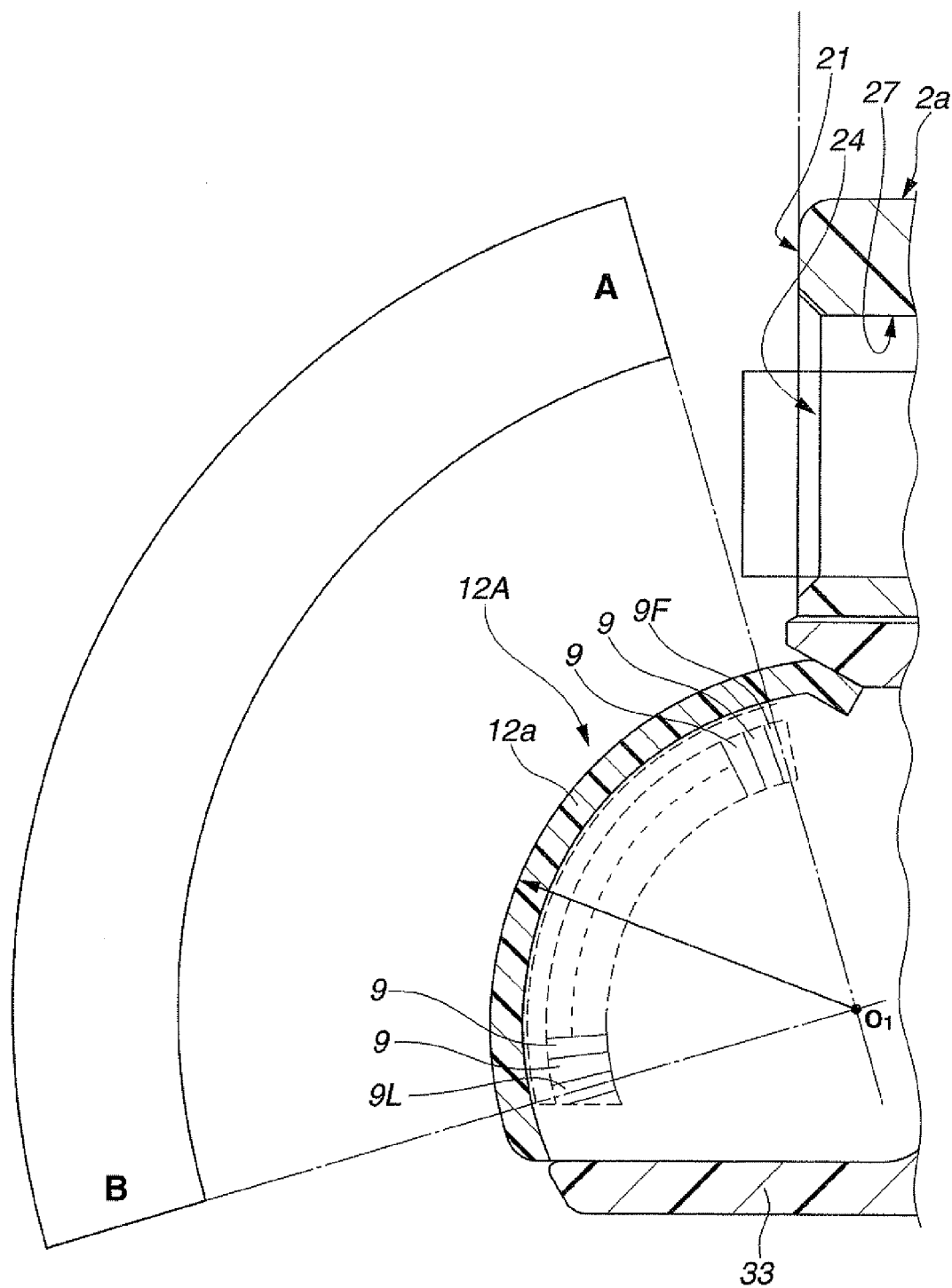
FIG. 12 is a sectional view taken along the XII-XII line of FIG. 11.

More specifically, the elevation widths of the ultrasound transducers 9 are set to be continuously and gradually narrower toward the final ultrasound transducer 9L from the first ultrasound transducer 9F, namely, toward B from A in FIG. 12. Accordingly, as shown in FIG. 11, the ultrasound probe 12A is formed to be compact as compared with the ultrasound probe 12 of FIG. 3, which is shown by the two-dot chain line in FIG. 11, and formed into a trapezoidal shape seen from the front.

In the ultrasound unit 10A configuring the ultrasound probe 12A like this, as the elevation width becomes narrower, the ultrasound beam which is irradiated easily diffuses and sensitivity is reduced theoretically.

However, in the present embodiment, by setting the shape of the nose piece 11A to be small in accordance with a change of the elevation width of the ultrasound probe 12A, the nose piece 11A becomes small as compared with the outer shape of the nose piece 11 of FIG. 3 shown by the two-dot chain line, and reduction in the diameter of the distal end portion of the endoscope 1 can be realized. Accordingly, insertability of the endoscope can be improved.

Figure 13:
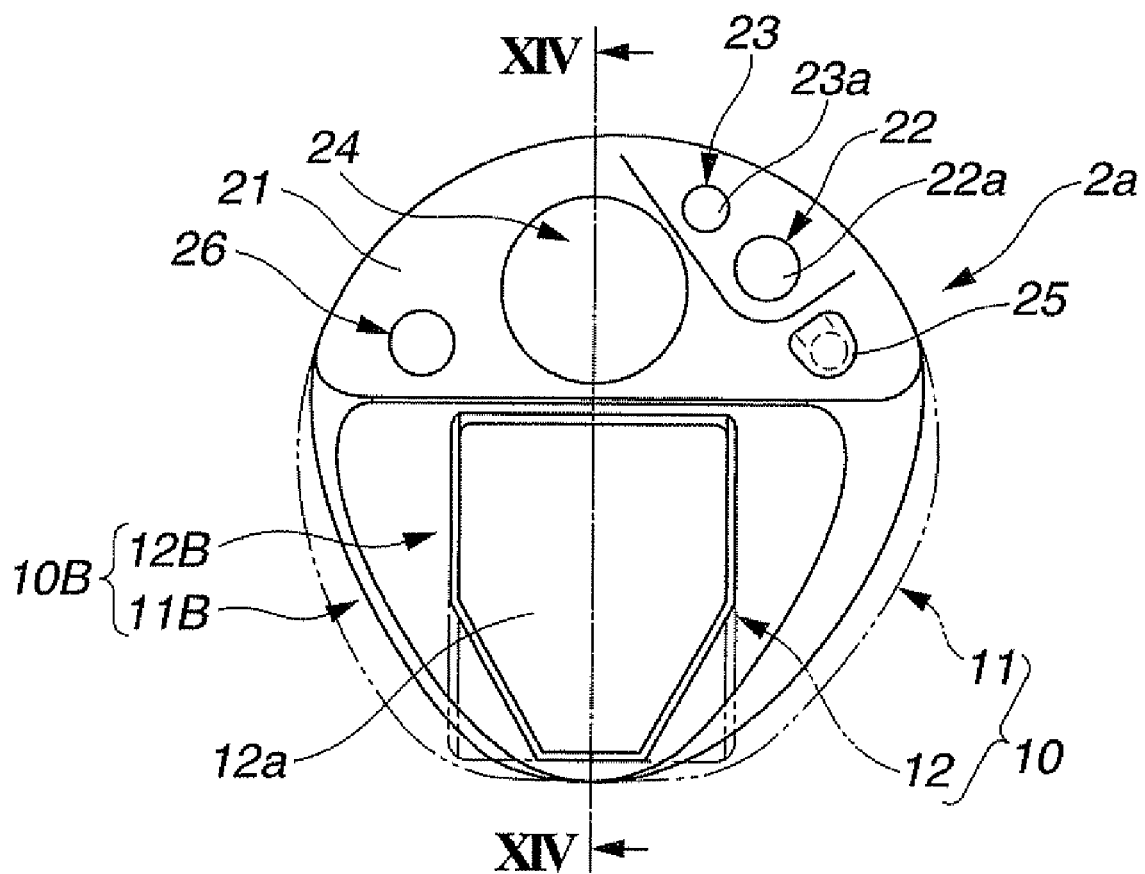
FIG. 13 is a front view of the distal end portion including an ultrasound probe including a portion in which a part of the elevation width continuously changes, seen from the front.
Figure 14:
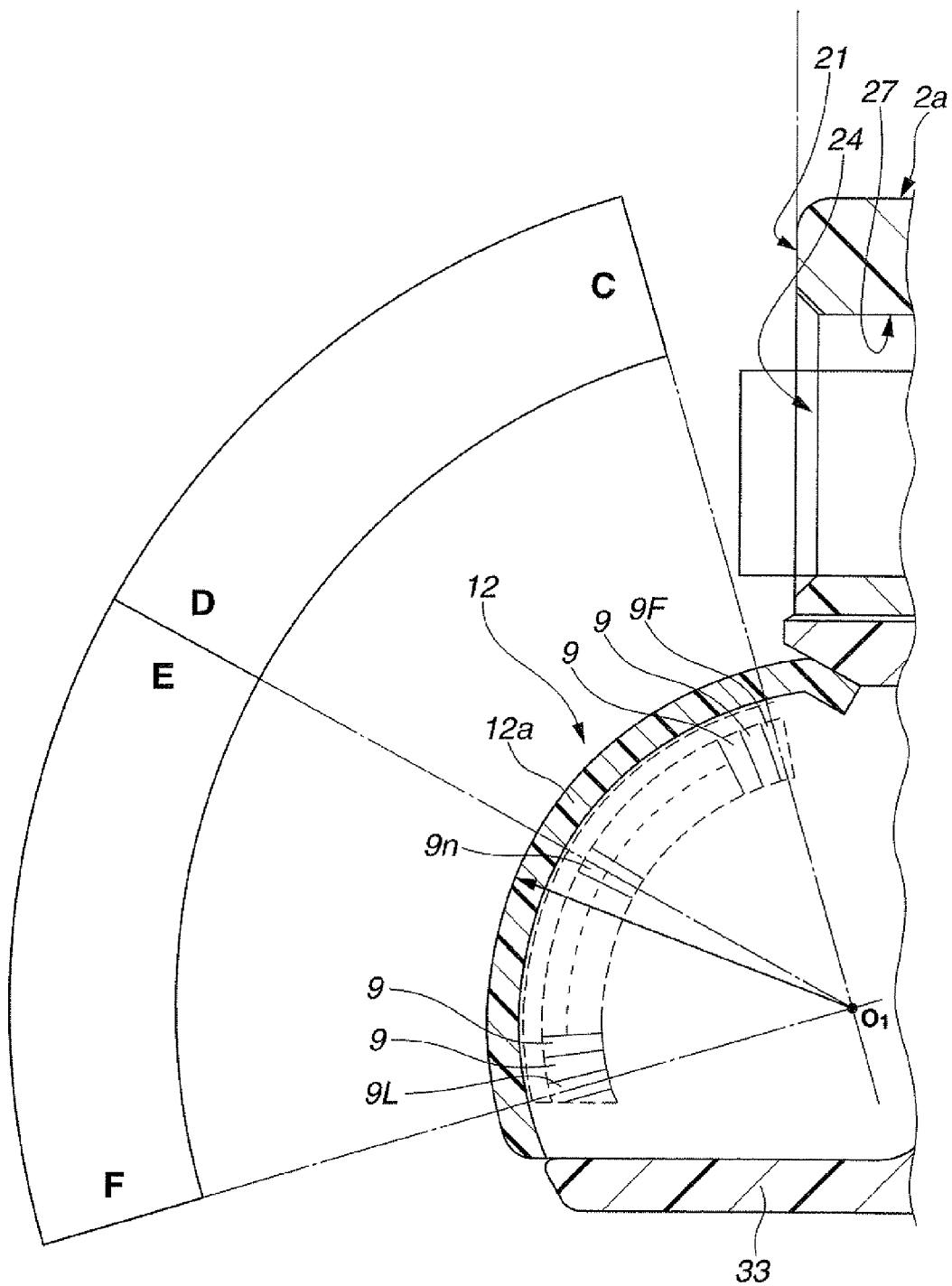
FIG. 14 is a sectional view taken along the XIV-XIV line of FIG. 13.

In an ultrasound probe 12B with a configuration shown in FIGS. 13 and 14, the first ultrasound transducer 9F to the $n^{th}$ ultrasound transducer 9n are set to have the same dimensions. Specifically, the elevation width in a range from C to D in FIG. 14 is uniformly set at W. On the other hand, the $(n+1)^{th}$ ultrasound transducer 9(n+1) and the final ultrasound transducer 9L differ in elevation width. More specifically, toward the final ultrasound transducer 9L from the $(n+1)^{th}$ ultrasound transducer 9(n+1), in other words, toward F from E in FIG. 14, the elevation widths of the ultrasound transducers 9 are set to be gradually narrower. Accordingly, as shown in FIG. 13, the ultrasound probe 12B is formed to be compact as compared with the ultrasound probe 12 shown in FIG. 3 shown by the two-dot chain line and formed into the shape of a home base of baseball seen from the front.

Thereby, the nose piece 11B is made smaller as compared with the outer shape of the nose piece 11 shown in FIG. 3 shown by the two-dot chain line, and reduction in the diameter of the distal end portion of the endoscope 1 can be realized. Further, in the ultrasound unit 10B configuring the ultrasound probe 12B, the elevation width has the same dimension in the range from A to B, and therefore, an ultrasound image with the similar image quality to the ultrasound unit 10 can be obtained.

The present invention is not limited only to the embodiment described above, but various modifications may be made in the range without departing from the spirit of the invention.

What is claimed is:

1. An ultrasound endoscope having an ultrasound probe portion disposed at a distal end side of a distal end rigid portion configuring a distal end of a flexible tube portion, a bending portion and the distal end rigid portion configuring an endoscope insertion portion, and a treatment instrument outlet formed at a distal surface of the distal end rigid portion, the ultrasound probe comprising:

a plurality of ultrasound transducers arranged in a convex circular arc shape, a center of curvature of the plurality of ultrasound transducers being disposed at a position proximal to a line orthogonal to an endoscope insertion axis and contacting a distal surface of the treatment instrument outlet.

2. The ultrasound endoscope according to claim 1, wherein a center axis of a sound ray of a first ultrasound transducer disposed at a position which is the closest to the treatment instrument outlet, out of the plurality of ultrasound transducers, is set to be inclined in a distal end direction by an angle which does not exceed 90 degrees, with respect to the endoscope insertion axis.

3. The ultrasound endoscope according to claim 2, wherein the distal end rigid portion includes a distal end surface which becomes a plane substantially perpendicular to the endoscope insertion axis, at the distal end side, and the treatment instrument outlet is provided in the distal end surface.

4. The ultrasound endoscope according to claim 3, wherein an angle formed by the center axis of the sound ray of the first ultrasound transducer and the endoscope insertion axis is set so as not exceed an angle formed by the distal end surface and the endoscope insertion axis, and the center axis of the sound ray is inclined in the distal end direction from the distal end surface.

5. The ultrasound endoscope according to claim 3, wherein relationship between an angle θ1 formed by the center axis of the sound ray of the first ultrasound transducer and the distal end surface and a spread angle θ2 of ultrasound irradiated from the first ultrasound transducer is set to be relationship of at least θ1>θ2/2.

6. The ultrasound endoscope according to claim 1, wherein a center axis in a longitudinal direction of the treatment instrument inserting channel is set to be substantially parallel with the endoscope insertion axis.

7. The ultrasound endoscope according to claim 1, wherein a center axis of a sound ray of a final ultrasound transducer which is the farthest from the treatment instrument outlet, out of the plurality of ultrasound transducers is set to be substantially parallel with the endoscope insertion axis.

8. The ultrasound endoscope according to claim 1, wherein in the plurality of ultrasound transducers arranged in the circular arc shape, a first sector formed by the circular arc, the center axis of the sound ray of the final ultrasound transducer and the endoscope insertion axis does not overlap with a second sector formed by the circular arc, a center axis of a sound ray oscillated by the first ultrasound transducer and the endoscope insertion axis.

9. The ultrasound endoscope according to claim 1, wherein elevation widths of the plurality of ultrasound transducers arranged in the circular arc shape have the same dimensions, or are narrower at the distal end side than a treatment instrument outlet side.

* * * * *